United States Patent
Ikeda et al.

(10) Patent No.: US 8,796,301 B2
(45) Date of Patent: Aug. 5, 2014

(54) THERAPEUTIC OR PROPHYLACTIC AGENT FOR DYSKINESIA

(75) Inventors: Ken Ikeda, Kamakura (JP); Hidenori Mochizuki, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 438 days.

(21) Appl. No.: 12/597,442

(22) PCT Filed: Apr. 24, 2008

(86) PCT No.: PCT/JP2008/057930
§ 371 (c)(1),
(2), (4) Date: Nov. 30, 2009

(87) PCT Pub. No.: WO2008/133297
PCT Pub. Date: Nov. 6, 2008

(65) Prior Publication Data
US 2010/0130524 A1     May 27, 2010

(30) Foreign Application Priority Data
Apr. 24, 2007 (JP) ................................. 2007-114309

(51) Int. Cl.
*A01N 43/42* (2006.01)
*A61K 31/44* (2006.01)
*C07D 489/00* (2006.01)

(52) U.S. Cl.
USPC ........................................................ 514/282

(58) Field of Classification Search
USPC ............................................ 514/282; 546/44
See application file for complete search history.

(56) References Cited

U.S. PATENT DOCUMENTS

| 6,153,620 A | 11/2000 | Kornetsky |
| 2001/0044449 A1 | 11/2001 | Nagase et al. |
| 2005/0245587 A1 | 11/2005 | Brotchie et al. |

FOREIGN PATENT DOCUMENTS

| EP | 1380306 A1 | 1/2004 |
| JP | 6-505747 A | 6/1994 |
| JP | 2003-512428 A | 4/2003 |
| WO | WO-99/11289 A1 | 3/1999 |
| WO | WO 00/03715 A1 | 1/2000 |

OTHER PUBLICATIONS

Henry et al. "mu- and delta-Opioid Receptor Antagonists Reduce Levodopa-Induced Dyskinesia in the MPTP-Lesioned Primate Model of Parkinson's Disease", Experimental Neurology, 2001, vol. 171, pp. 139-146.*
Mizoguchi et al. "Blockade of mu-opioid receptor-mediated G-protein activation and antinociceptin by TRK-820 in mice", European Journal of Pharmacology, 2003, vol. 461, pp. 35-39.*
Marin et al. "Effect of acute and chronic administration of U50,488, a kappa opioid receptor agonist, in 6-OHDA-lesioned rats chronically treated with levodopa", Experimental Neurology, 2003, vol. 183, pp. 66-73.*
Konitsiotis et al. "Levodopa-induced dyskinesia and rotational behavior in hemiparkinsonian rats: Independent featuers or components of the same phenomenon?", Behavioural Brain Research, Apr. 18, 2006, vol. 170, pp. 337-341.*
Brown et al., "Recent advances in the treatment of L-DOPA-induced dyskinesia", IDrugs, vol. 5, No. 5, 2002, pp. 454-468, XP-001156095.
Cox et al., "The selective K-opioid receptor agonist U50,488 reduces L-dopa-induced dyskinesias but worsens parkinsonism in MPTP-treated primates", Experimental Neurology, vol. 205, 2007, pp. 101-107, XP22396775A.
Extended European Search Report, dated Jul. 11, 2011, for European Application No. 08752029.2.
Ikeda et al., "Effects of TRK-820, a selective K-opioid receptor agonist, in the Parkinson's disease and dyskinesic model rats", Journal of Pharmacological Sciences, vol. 106, 2008, p. 236P, XP008138403.
Ikeda et al., "TRK-820, a selective kappa opioid receptor agonist, could effectively ameliorate L-DOPA-induced dyskinesia symptoms in a rat model of Parkinson's disease", European Journal of Pharmacology, vol. 620, 2009, pp. 42-48, XP0026626005.
Müller et al., "Levodopa, motor fluctuations and dyskinesia in Parkinson's disease", Expert Opin Pharmacother, vol. 7, No. 13, 2006, pp. 1715-1730, XP008138440.

* cited by examiner

*Primary Examiner* — Kendra D Carter
(74) *Attorney, Agent, or Firm* — Birch, Stewart, Kolasch & Birch, LLP

(57) ABSTRACT

An object of the present invention is to provide a drug with a high therapeutic or prophylactic effect on dyskinesia, without accompanying aggravation of symptoms of the primary disease, and with fewer side effects.
Accordingly, the present invention provides a therapeutic or prophylactic agent for dyskinesia, comprising as an effective component a compound having a 4,5-epoxy morphinan skeleton, which compound is represented by the Formula (I) below, or a pharmaceutically acceptable acid addition salt thereof:

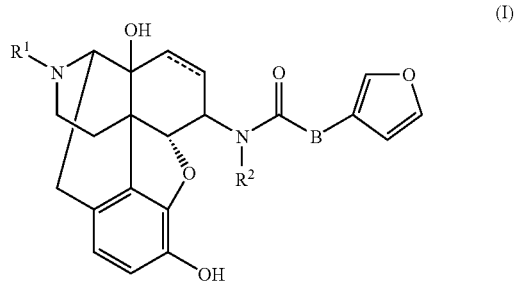

[wherein the double line composed of a dashed line and a solid line represents a double bond or single bond, $R^1$ is $C_4$-$C_7$ cycloalkylalkyl, $R^2$ is $C_1$-$C_5$ straight or branched alkyl, and B is —CH=CH—.]

4 Claims, 2 Drawing Sheets

THERAPEUTIC OR PROPHYLACTIC AGENT FOR DYSKINESIA

TECHNICAL FIELD

The present invention relates to a therapeutic or prophylactic agent for dyskinesia comprising as an effective component a morphinan derivative or a pharmaceutically acceptable acid addition salt thereof.

BACKGROUND ART

Dyskinesia is an abnormal movement involuntarily appearing on the four limbs and face. Representative symptoms thereof include tongue rolling, neck torsion, hip rocking as well as bending and stretching of arms and legs. Once dyskinesia appears, normal motor functions are impaired and thus a patient is forced to have a restricted life.

It has been known that dyskinesia is induced mainly as a side effect of long term administration of a drug such as a therapeutic agent for schizophrenia or Parkinson's disease. For instance, long term use of the therapeutic agent for schizophrenia induces particularly dyskinesia of the mouth and/or tongue and a therapeutic agent for Parkinson's disease, L-DOPA, also causes dyskinesia, both of which are well-known cases. Because the abnormal dyskinesia movements occur at any place and a patient who has a fear of being seen such symptoms by others avoids going out of the house, so that the quality of life of the patient is decreased, which is also problematic.

Known methods for treating or preventing dyskinesia include a method wherein the onset of dyskinesia is prevented by reducing L-DOPA dose as much as possible in a treatment for Parkinson's disease; a method wherein the therapy is carried out with a selective dopamine D2 receptor antagonist such as tiapride, an NMDA receptor antagonist such as amantadine, or a muscle relaxant such as a botulinus toxin; and a method wherein the onset of dyskinesia is prevented by avoiding a long term irresponsibly administration of a large amount of a therapeutic agent for schizophrenia. There are not however effective therapeutic or prophylactic methods and thus urgent development of a treating agent or prophylactic agent is desired.

Meanwhile, it has been recently reported that an opioid κ receptor agonist, U50488 (trans-(±)-(3,4-dichlorophenyl)-N-methyl-N-[2-(1-pyrrolidin-1-yl)-cyclohexyl]acetamide) suppresses L-DOPA-induced dyskinesia while deteriorates Parkinson's symptoms (Non-patent Literature 1: Cox H et al., *Exp Neural.* 2007, Volume 205, Issue 1, p.101-107). Patent Literature 1 describes that β-funaltrexamine (β-FNA), albeit an opioid μ antagonist, which is a compound having a morphinan skeleton and close to the effective component used in the present application in terms of a chemical structure, suppresses dyskinesia (Patent Literature 1: WO00/003715). Meanwhile, the compound used as effective component in the present application is described with its analgesic action, diuresis action and opioid κ agonist activity in Patent Literature 2. In addition, its antitussive action and its use as brain cell protective agent, antipruritic drug, therapeutic agent for hyponatremia, ORL-1 receptor antagonist, therapeutic agent for neuropathic pain, antipruritic drug for tunica conjunctiva, therapeutic agent for neuropsychiatric disorder, therapeutic agent for septicemia and antipruritic drug for multiple sclerosis are described in patent literatures (Patent Literatures 3 to 12: WO 95/001178, WO 95/003307, WO 98/023290, WO 99/005146, Japanese Laid-open Patent Application (Kokai) No. 2000-53572, WO 01/014383, Japanese Laid-open Patent Application (Kokai) No. 2001-163784, WO 02/078744, WO 02/089845, and WO 06/095836). In particular, the patent literature disclosing the use of the compound as a brain cell protective agent also describes its effect on Parkinson's disease but does not disclose its effectiveness against dyskinesia at all.

Dyskinesia occurs as a side effect of a drug therapy for Parkinson's disease, schizophrenia or the like, and is generally aggravated by continuous administration of a therapeutic agent. On the other hand, as described in Non-patent Literature 1 (Cox H et al., *Exp Neurol.*, 2007, Volume 205, Issue 1, p. 101-107), a drug having a therapeutic effect on dyskinesia is thought to cause aggravation of the primary disease. Thus a fact that a drug effective on the primary disease has a therapeutic effect on dyskinesia can be said to be against a common technical knowledge.

Non-patent Literature 1: Cox H et al, *Exp Neurol.* 2007, Volume 205, Issue 1, p. 101-107

Patent Literature 1: WO 00/003715

Patent Literature 2: WO 93/015081

Patent Literature 3: WO 95/001178

Patent Literature 4: WO 95/003307

Patent Literature 5: WO 98/023290

Patent Literature 6: WO 99/005146

Patent Literature 7: Japanese Laid-open Patent Application (Kokai) No. 2000-53572

Patent Literature 8: WO 01/014383

Patent Literature 9: Japanese Laid-open Patent Application (Kokai) No. 2001-163784

Patent Literature 10: WO 02/078744

Patent Literature 11: WO 02/089845

Patent Literature 12: WO 06/095836

DISCLOSURE OF INVENTION

Problems to be Solved by the Invention

It is an object of the present invention to provide a drug with a high therapeutic or prophylactic effect on dyskinesia, without accompanying aggravation of symptoms of the primary disease, and with fewer side effects.

Means for Solving the Problems

In order to solve the above described problem, the present inventors intensively studied to discover that a specific compound having a 4,5-epoxy morphinan skeleton or a pharmaceutically acceptable acid addition salt thereof is useful as a therapeutic and prophylactic agent for dyskinesia, which agent has markedly high effects, no concerns of causing aggravation of symptoms of the primary disease, and fewer side effects, thereby completing the present invention.

Accordingly, the present invention relates to the following [1] to [5].

[1] A therapeutic or prophylactic agent for dyskinesia, comprising as an effective component a compound represented by the Formula (I) below or a pharmaceutically acceptable acid addition salt thereof:

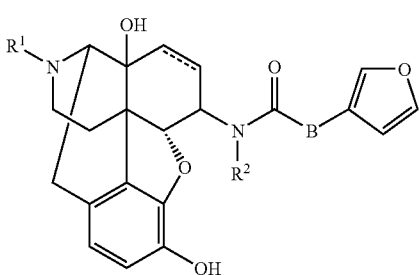

wherein the double line composed of a dashed line and a solid line represents a double bond or a single bond, $R^1$ is $C_4$-$C_7$ cycloalkylalkyl, $R^2$ is $C_1$-$C_5$ straight or branched alkyl, and B is —CH=CH—.

[2] The therapeutic or prophylactic agent for dyskinesia described in [1], wherein in said Formula (I), $R^1$ is cyclopropylmethyl and $R^2$ is methyl.

[3] The therapeutic or prophylactic agent for dyskinesia described in, wherein said compound represented by said Formula (I) is (−)-17-(cyclopropylmethyl)-3,14β-dihydroxy-4,5α-epoxy-6β-[N-methyl-trans-3-(3-furyl)acrylamido]morphinan.

[4] Use of a compound represented by the Formula (I) below or a pharmaceutically acceptable acid addition salt thereof for the production of a therapeutic or prophylactic agent for dyskinesia:

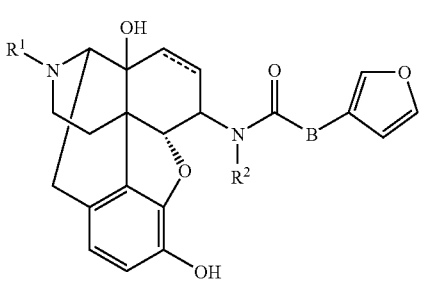

wherein the double line composed of a dashed line and a solid line represents a double bond or a single bond, $R^1$ is $C_4$-$C_7$ cycloalkylalkyl, $R^2$ is $C_1$-$C_5$ straight or branched alkyl, and B is —CH=CH—.

[5] A method for treating or preventing dyskinesia, comprising administrating an effective amount of a compound represented by the Formula (I) below or a pharmaceutically acceptable acid addition salt thereof to a patient in need of treatment or prophylaxis of dyskinesia:

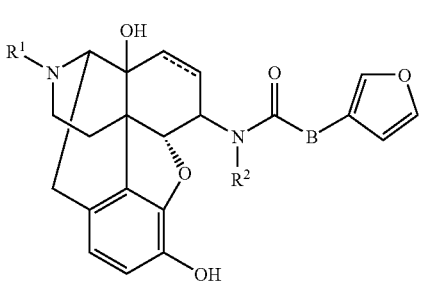

wherein the double line composed of a dashed line and a solid line represents a double bond or a single bond, $R^1$ is $C_4$-$C_7$ cycloalkylalkyl, $R^2$ is $C_1$-$C_5$ straight or branched alkyl, and B is —CH=CH—.

Effects of the Invention

By the present invention, a therapeutic or prophylactic agent for dyskinesia, for which effective therapeutic method or prophylactic method were hitherto not present, can be provided. The therapeutic or prophylactic agent for dyskinesia according to the present invention has an excellent alleviating effect on dyskinesia without accompanying aggravation of symptoms of the primary disease, which is its side effect. Accordingly, because dyskinesia alone is alleviated without aggravating the symptoms of the primary disease by administrating the therapeutic or prophylactic agent for dyskinesia according to the present invention to a patient with the onset of dyskinesia, the quality of life of the patient can be expected to be improved.

BEST MODE FOR CARRYING OUT THE INVENTION

Figure 1:
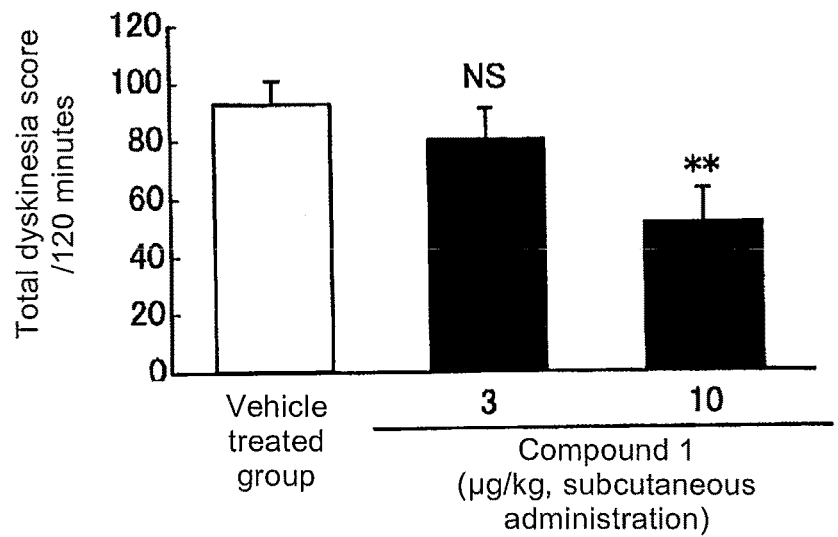
FIG. 1 is a graph showing the effect of Compound 1 on dyskinesia induced by L-DOPA in a rat model of Parkinson's disease, in Example 1.

The therapeutic agent or prophylactic agent for dyskinesia according to the present invention comprises as an effective component a compound represented by the Formula (1) and a pharmaceutically acceptable acid addition salt thereof:

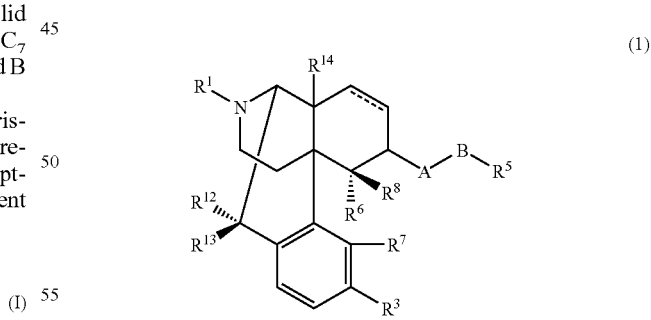

[wherein the double line composed of a dashed line and a solid line represents a double bond or a single bond.

$R^1$ represents $C_1$-$C_5$ alkyl, $C_4$-$C_7$ cycloalkylalkyl, $C_5$-$C_7$ cycloalkenylalkyl, $C_6$-$C_{12}$ aryl, $C_7$-$C_{13}$ aralkyl, $C_4$-$C_7$ alkenyl, allyl, furan-2-yl alkyl (wherein the number of carbon atoms in the alkyl moiety is 1 to 5) or thiophen-2-yl alkyl (wherein the number of carbon atoms in the alkyl moiety is 1 to 5).

$R^{14}$ represents hydrogen, hydroxy, nitro, $C_1$-$C_5$ alkanoyloxy, $C_1$-$C_5$ alkyl, or $NR^9R^{10}$, wherein $R^9$ represents hydrogen or $C_1$-$C_5$ alkyl; $R^{10}$ represents hydrogen, $C_1$-$C_5$ alkyl, or —C(=O)$R^{11}$, and $R^{11}$ represents hydrogen, phenyl, or $C_1$-$C_5$ alkyl.

$R^3$ represents hydrogen, hydroxy, $C_1$-$C_5$ alkanoyloxy or $C_1$-$C_5$ alkoxy.

A represents —XC(=Y)—, —XC(=Y)Z—, —X— or —XSO$_2$— (wherein X, Y and Z independently represent $NR^4$, S or O, wherein $R^4$ represents hydrogen, $C_1$-$C_5$ straight or branched alkyl or $C_6$-$C_{12}$ aryl, and in cases where more than one $R^4$ are present in the formula, $R^4$s may be the same or different).

B represents valence bond, $C_1$-$C_{14}$ straight or branched alkylene (wherein the alkylene may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and wherein 1 to 3 methylene groups therein may be replaced with carbonyl group(s)), $C_2$-$C_{14}$ straight or branched acyclic unsaturated hydrocarbon containing 1 to 3 double bonds and/or triple bonds (wherein the acyclic unsaturated hydrocarbon may have at least one substituent selected from the group consisting of $C_1$-$C_5$ alkoxy, $C_1$-$C_5$ alkanoyloxy, hydroxy, fluorine, chlorine, bromine, iodine, amino, nitro, cyano, trifluoromethyl and phenoxy, and that 1 to 3 methylene groups in the acyclic unsaturated hydrocarbon may be replaced with carbonyl group(s)), or $C_1$-$C_{14}$ straight or branched saturated or unsaturated hydrocarbon containing 1 to 5 thioether bonds, ether bonds and/or amino bonds (wherein a hetero atom does not directly binds to A, and 1 to 3 methylene groups are optionally replaced with carbonyl group(s)).

$R^5$ represents hydrogen or an organic group having a skeleton selected from those shown below:

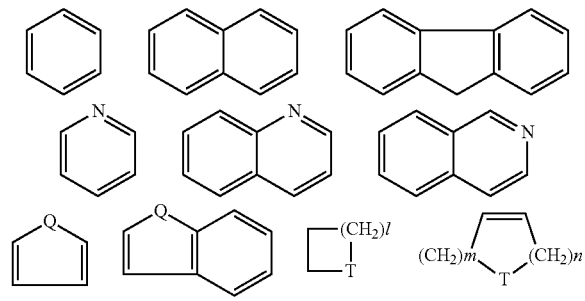

Q: N, O, S
T: $CH_2$, NH, S, O
l = 0-5
m, n ≧ 0
m + n ≦ 5

Organic Groups Represented by $R^5$ (wherein Q represents N, O or S; T represents $CH_2$, NH, S or O; l represents an integer of 0 to 5; and m and n independently represent integers of 0 to 5, the total of m and n being not more than 5; each of the organic groups may have at least one substituent selected from the group consisting of $C_1$-$C_5$ alkyl, $C_1$-$C_5$ alkoxy, $C_1$-$C_5$ alkanoyloxy, hydroxy, fluorine, chlorine, bromine, iodine, amino, nitro, cyano, isothiocyanato, trifluoromethyl, trifluoromethoxy and methylenedioxy).

$R^6$ represents hydrogen; $R^7$ represents hydrogen, hydroxy, $C_1$-$C_5$ alkoxy or $C_1$-$C_5$ alkanoyloxy; or $R^6$ and $R^7$ together represent —O—, —$CH_2$— or —S—.

$R^8$ represents hydrogen, $C_1$-$C_5$ alkyl or $C_1$-$C_5$ alkanoyl.

$R^{12}$ and $R^{13}$ both represent hydrogen, or one of them represents hydrogen and the other represents hydroxy, or they together represent oxo.

The Formula (1) includes (+), (−) and (±) isomers.]

The double line composed of a dashed line and a solid line in the Formula (1) represents a double bond or single bond with the latter being preferred.

Among the compounds represented by the Formula (1), the therapeutic agent or prophylactic agent for dyskinesia according to the present invention preferably comprises as an effective component the compound represented by the already shown Formula (I) or the pharmaceutically acceptable acid addition salt thereof. The double line composed of a dashed line and a solid line in the Formula (I) represents a double bond or a single bond with the latter being preferred.

In the Formula (I), $R^1$ represents $C_4$-$C_7$ cycloalkylalkyl. Among them, $R^1$ is preferably cyclopropylmethyl, cyclobutylmethyl, cyclopentylmethyl or cyclohexylmethyl, more preferably cyclopropylmethyl.

$R^2$ represents $C_1$-$C_5$ straight or branched alkyl. $R^2$ is preferably methyl, ethyl or propyl. Among them, methyl is more preferred.

B represents —CH=CH—. B is preferably trans-form —CH=CH—.

The compound represented by the Formula (I) is preferably a compound wherein $R^1$ is cyclopropylmethyl and $R^2$ is methyl, more preferably (−)-17-(cyclopropylmethyl)-3,14β-dihydroxy-4,5α-epoxy-6β-[N-methyl-trans-3-(3-furyl)acrylamido]morphinan but the present invention is not limited thereto.

The compounds represented by the Formula (I) may be produced by the method described in Japanese Patent No. 2525552. Among the compounds represented by the Formula (1), the compounds wherein both $R^{12}$ and $R^{13}$ are hydrogen may be produced by the method described in Japanese Patent No. 2525552. Among the compounds represented by the Formula (1), the compounds wherein $R^{12}$ and $R^{13}$ cooperatively represent oxo may be, for instance, produced by the method described in *Chem. Pharm. Bull.*, 52, 664(2004) and Japanese Patent No. 2525552 using a compound having 10-oxo obtained in accordance with literatures (*Heterocycle*, 63, 865 (2004); *Bioorg. Med. Chem. Lett.*, 5, 1505(1995)) as a raw material. In addition, among the compound represented by the Formula (1), the compounds wherein $R^{12}$ is hydroxyl and $R^{13}$ is hydrogen may be produced by the method described in *Chem. Pharm. Bull.*, 52, 664(2004).

Examples of the pharmaceutically acceptable acid addition salts according to the present invention include inorganic acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzenesulfonic acid salt, p-toluenesulfonic acid salt and camphorsulfonic acid salt. Among these, hydrochloric acid salt, hydrobromic acid salt, phosphoric acid salt, tartaric acid salt, methanesulfonic acid salt or the like is preferred, but the acid addition salt is of course not limited thereto.

The compound represented by Formula (I) or the pharmaceutically acceptable acid addition salt thereof may be administered orally as they are or in the form of pharmaceutical compositions after being admixed with known pharmaceutically acceptable acids, carriers or vehicles, after being purified to the level suitable for medical use and after passing the requisite safety tests. The formulation for the oral administration can be selected from tablet, capsule, powder, pellet, and the like but is of course not limited thereto.

The content of the compound presented by the Formula (I) or the pharmaceutically acceptable acid addition salt thereof in a pharmaceutical composition is not restricted and may be usually 0.1 μg to 100 mg per a single administration. The administration dose may be appropriately selected depending on symptoms, age, and body weight of the patient, administration route and the like, and usually about 0.1 μg to 20 mg in terms of the amount of the compound represented by the Formula (I), preferably about 1 μg to 10 mg may be administrated to an adult per day in one time or dividedly in several times.

The compound according to the present invention, that is, the compound represented by the Formula (I) or the pharmaceutically acceptable acid addition salt can be used as a monotherapy or as an auxiliary agent for other therapeutic agents for treating or preventing dyskinesia. For example, the compound according to the present invention can be used for treating or preventing side effects induced by a therapeutic agent for Parkinson's disease or therapeutic agent for schizophrenia. Examples of the therapeutic agent to be administrated to a parkinsonian patient include, but not limited to, L-DOPA such as levodopa; aromatic L-amino decarboxylase inhibitors such as carbidopa and benserazide; dopamine receptor agonists such as bromocriptine, pergolide, talipexole, cabergoline and pramipexole; monoamine oxidase inhibitors such as selegiline; adenosine A2A receptor antagonists such as istradefylline; anticholinergic agents such as trihexyphenidyl, biperiden, and profenamine; and catechol-O-methyltransferase inhibitors such as tolcapone or entacapone. Examples of the therapeutic agent to be administrated to a patient with schizophrenia include, but not limited to, typical antipsychotics such as chlorpromazine, fluphenazine, haloperidol, loxapine, mesoridazine, molindone, perphenazine, pimozide, thioridazine, thothixene and trifluoperazine; and atypical antipsychotics such as aripiprazole, clozapine, olanzapine, quetiapine, risperidone and ziprasidone. Furthermore, the compound according to the present invention can be administrated in combination with other therapeutic agents for reducing dyskinesia. Examples thereof include selective dopamine D2 receptor antagonists such as tiapride; opioid μ receptor antagonists such as clocinnamox, isothiocyanic acid etonitazeny β-funaltrexamine, naloxonazine and cyprodime; α2-adrenalin receptor antagonists such as yohimbine; cannabinoids CB1 antagonists such as rimonabant; NMDA receptor antagonists such as amantadine; histamine H3 receptor agonists such as imetit; and muscle relaxants such as botulinus toxin. The therapeutic or prophylactic agent according to the present invention can also be administrated in combination with a therapeutic method for Parkinson's disease or psychiatric disorders, such as deep electrical stimulation. These administration modes are given as examples and should not be interpreted to limit the present invention.

EXAMPLES

The present invention will now be described more concretely by way of Examples thereof.

Example 1

Effect of (−)-17-(cyclopropylmethyl)-3,14β-dihydroxy-4,5α-epoxy-6β-[N-methyl-trans-3-(3-furyl)acrylamido]morphinan hydrochloride (Compound 1) on L-DOPA-induced dyskinesia in a rat model of Parkinson's disease.

It has been reported that abnormal involuntary movements induced by repeated administration of L-DOPA to a rat model of Parkinson's disease, which rat was generated by infusing 6-hydroxydopamine into one side of the substantia nigra-corpus striatum of a rodent, are dyskinesia manifesting as a side effect when a parkinsonian patient took L-DOPA for a long period of time (Lundblad M et al., *Eur. J. Neurosci.* 15:120, 2002).

In this test, six-week old male rats (strain name: CRJ:CD (SD)IGS) were purchased from Charles River Laboratories Japan. After habituation breeding for not less than six days, the rats were used at the age of seven or eight weeks. The rats were anesthetized with pentobarbital sodium (40 mg/kg, intraperitoneal administration) and then 8 μg of 6-hydroxydopamine hydrobromate (hereinafter referred to as "6-hydroxydopamine" for short) was injected to the left medial forebrain bundle over three minutes to destroy the one side (left side) of the substantial nigra-corpus striatum dopaminergic nerve cells. In physiological saline containing 0.05% ascorbic acid, 6-hydroxydopamine was dissolved to 8 μg/2 μL. For the purpose of protecting noradrenergic nerve cells, desipramine hydrochloride (25 mg/kg) was intraperitoneally administrated 30 minutes before the surgery. Seven days after the injection of 6-hydroxydopamine, L-DOPA (40 mg/kg, oral administration) was administrated once a day (on a day when the behavior observation was carried out, dividedly twice a day via oral administration; 20 mg/kg at the behavior observation and 20 mg/kg after the behavior observation). Repeated administration was carried out at a frequency of not less than five days a week for three weeks to induce dyskinesia. With regard to evaluation of dyskinesia, the following four behaviors were employed as indices.

1. Presence of rotating behaviors: rotating behaviors toward the side contralateral to the side where 6-hydroxydopamine was infused.
2. Body: posture bending toward the side contralateral to the side where 6-hydroxydopamine was infused, which posture is originated from dysmyotonia of the neck or upper body
3. Arms: abnormal movements which the upper limb of the side contralateral to the side where 6-hydroxydopamine was infused moves aimlessly.
4. Mouth: aimless mouth movements and tongue protrusion Classification of the behaviors above was scored by the scoring scale of dyskinesia shown in Table 1 below.

TABLE 1

| Score | Scoring scale of dyskinesia |
|---|---|
| 0 | No dyskinesia is observed. |
| 1 | Dyskinesia is observed not more than 50% of the observation time. |
| 2 | Dyskinesia is observed not less than 50% of the observation time. |
| 3 | Dyskinesia is continuously observed during the observation time. (Sensory stimulus such as sound can interrupt dyskinesia.) |
| 4 | Dyskinesia is continuously observed during the observation time. (Sensory stimulus such as sound cannot interrupt dyskinesia.) |

The maximum score of dyskinesia for each evaluation item is, as shown in Table 1, four points respectively. For scoring, the observation was made for one minute per individual, which was repeated a total of 12 times. Each observation was repeated with a nine-minute interval. Accordingly, a total amount of time required to score is 120 minutes. Here, a possible maximum score per observation is 16 points, and, with the observation being repeated 12 times, a maximum total score per individual is 192 points. The observation was carried out by placing each rat separately in one section of an observation cage (one section: 30×30×36 cm).

For evaluation of test agent, the test was carried out using an identical individual. In other words, a score for dyskinesia upon administration of a vehicle for test agent and L-DOPA was obtained before administration of test agent. The obtained result was defined as a control score. Thereafter, test agent and L-DOPA were administrated. The effects of test agent on L-DOPA-induced dyskinesia were evaluated and the obtained score was compared with the control score.

A suppressive effect of Compound 1 for a rat in which dyskinesia was induced by L-DOPA was evaluated. Simultaneously with the administration of L-DOPA (20 mg/kg) orally, 3 or 10 μg/kg of Compound 1 was subcutaneously administrated to evaluate its effect on dyskinesia. As comparative compounds, β-funaltrexamine (10 or 30 mg/kg, subcutaneous administration) and U50488 (3 or 10 mg/kg, subcutaneous administration) were used.

The structure of Compound 1 is represented by the formula (II) below.

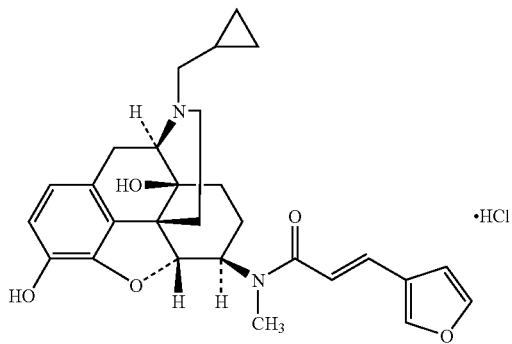

(II)

Figure 3:
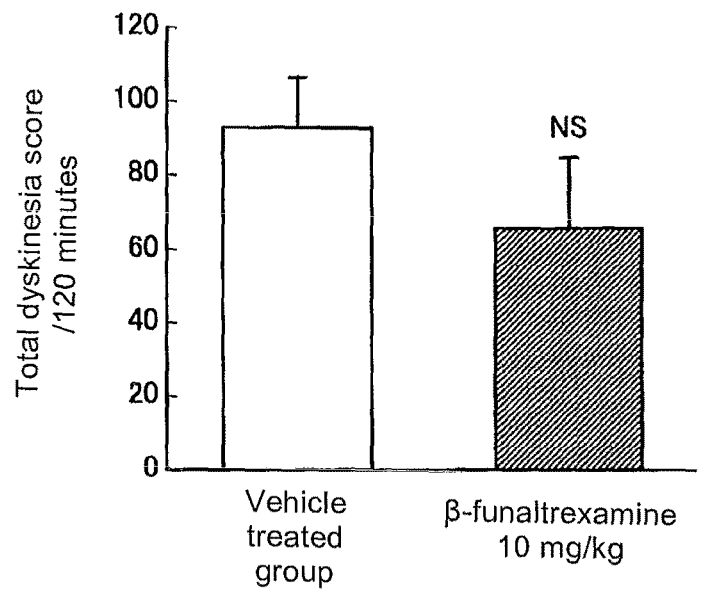
FIG. 3 is a graph showing the effect of β-funaltrexamine on dyskinesia induced by L-DOPA in a rat model of Parkinson's disease, in Example 1.
Figure 4:
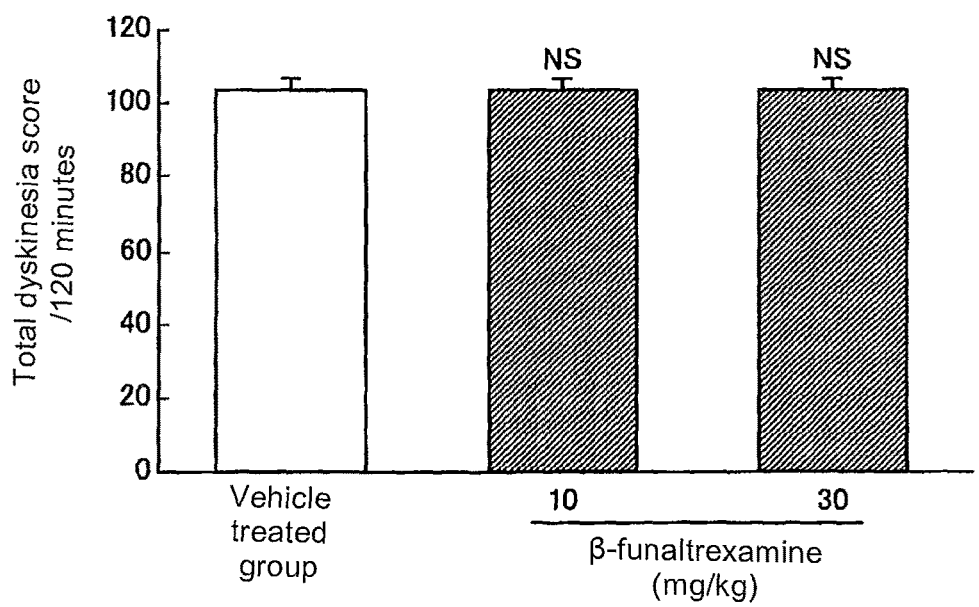
FIG. 4 is a graph showing the effect of β-funaltrexamine (10 and 30 mg/kg) on dyskinesia induced by L-DOPA in a rat model of Parkinson's disease, in Example 1.

As shown in FIG. 1, Compound 1 significantly suppressed dyskinesia at a dose of 10 μg/kg (n=7-8). With the compound U50488, which has the same opioid κ receptor agonist activity, there was no difference at 3 mg/kg whereas dyskinesia was significantly suppressed at a dose of 10 mg/kg (FIG. 2, n=7-8). β-funaltrexamine did not influence L-DOPA-induced dyskinesia at all at both doses of 10 and 30 mg/kg (FIG. 3, n=7-8, FIG. 4, n=4). These test results reveal that Compound 1 can suppress L-DOPA-induced dyskinesia by at the smallest dose.

Figure 2:
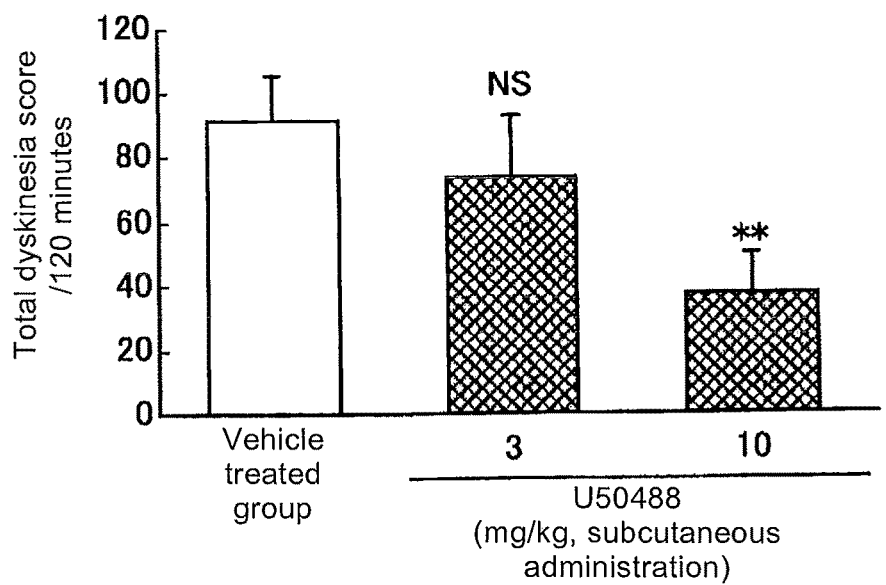
FIG. 2 is a graph showing the effect of U50488 on dyskinesia induced by L-DOPA in a rat model of Parkinson's disease, in Example 1.

In FIG. 1 and FIG. 2, the symbol "" indicates statistical significance at a significance level of not more than 1% with respect to the vehicle-treated group (subcutaneous administration). In FIG. 1, FIG. 2, FIG. 3, and FIG. 4**, NS indicates not statistically significant (parametric Williams' multiple comparison test).

The invention claimed is:

1. A method for treating dyskinesia, comprising administrating an effective amount of a compound represented by the Formula (I) below or a pharmaceutically acceptable acid addition salt thereof to a patient in need of treatment of dyskinesia:

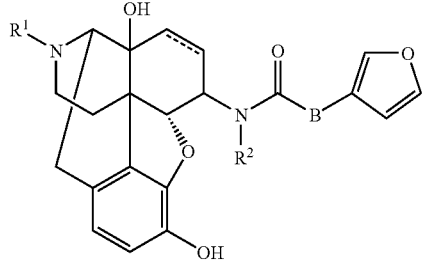

(I)

wherein the double line composed of a dashed line and a solid line represents a double bond or a single bond, $R^1$ is $C_4$-$C_7$ cycloalkylalkyl, $R^2$ is $C_1$-$C_5$ straight or branched alkyl, and B is —CH═CH—.

2. The method according to claim 1, wherein in said Formula (I), $R^1$ is cyclopropylmethyl and $R^2$ is methyl.

3. The method according to claim 1, wherein said compound represented by said Formula (I) is (−)-17-(cyclopropylmethyl)-3,14β-dihydroxy-4,5α-epoxy-6β-[N-methyl-trans-3-(3-furyl)acrylamide]morphinan.

4. The method according to claim 1, wherein the patient has Parkinson's disease.

* * * * *

UNITED STATES PATENT AND TRADEMARK OFFICE
CERTIFICATE OF CORRECTION

| | | |
|---|---|---|
| PATENT NO. | : 8,796,301 B2 | Page 1 of 1 |
| APPLICATION NO. | : 12/597442 | |
| DATED | : August 5, 2014 | |
| INVENTOR(S) | : Ikeda et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 554 days.

Signed and Sealed this
Eleventh Day of August, 2015

Michelle K. Lee
*Director of the United States Patent and Trademark Office*